US012614568B2

(12) United States Patent
Gras et al.

(10) Patent No.: US 12,614,568 B2
(45) Date of Patent: Apr. 28, 2026

(54) LOW-LATENCY VIDEO CAPTURE AND OVERLAY

(71) Applicant: DIGITAL SURGERY LIMITED, London (GB)

(72) Inventors: Gauthier Camille Louis Gras, London (GB); Petros Giataganas, London (GB)

(73) Assignee: DIGITAL SURGERY LIMITED, London (GB)

( * ) Notice: Subject to any disclaimer, the term of this patent is extended or adjusted under 35 U.S.C. 154(b) by 8 days.

(21) Appl. No.: 18/694,527

(22) PCT Filed: Oct. 21, 2022

(86) PCT No.: PCT/EP2022/079440
§ 371 (c)(1),
(2) Date: Mar. 22, 2024

(87) PCT Pub. No.: WO2023/067171
PCT Pub. Date: Apr. 27, 2023

(65) Prior Publication Data
US 2024/0395287 A1     Nov. 28, 2024

(30) Foreign Application Priority Data
Oct. 21, 2021     (GR) ............................... 20210100720

(51) Int. Cl.
G11B 27/036          (2006.01)
G06T 1/20          (2006.01)
(Continued)

(52) U.S. Cl.
CPC .............. G11B 27/036 (2013.01); G06T 1/20 (2013.01); G06T 11/60 (2013.01); G16H 30/40 (2018.01);
(Continued)

(58) Field of Classification Search
CPC ........ G11B 27/036; G16H 30/40; G06T 1/20; G06T 11/60; H04N 7/01; H04N 7/08
See application file for complete search history.

(56) References Cited

U.S. PATENT DOCUMENTS

2007/0156017 A1*  7/2007  Lamprecht ......... A61B 1/00194
                                                            600/102
2021/0019982 A1*  1/2021  Todd .................. H04N 21/2343
(Continued)

OTHER PUBLICATIONS

International Search Report and Written Opinion for Application No. PCT/EP2022/079440; International Filing Date: Oct. 21, 2022; Mailing date: Aug. 2, 2023; 11 pages.

*Primary Examiner* — Mishawn N. Hunter
(74) *Attorney, Agent, or Firm* — CANTOR COLBURN LLP; Robert Crist

(57)          ABSTRACT
Aspects include low latency video capture and overlay through video capture circuitry. Video input associated with a surgical procedure can be provided to one or more processing devices of a video processing system to analyze the video input. An overlay received from the one or more processing devices is combined with the video input to create a blended video output of the surgical procedure. The blended video output is output to a primary display using an interface having a lower latency than a secondary display output of the video processing system.

20 Claims, 10 Drawing Sheets

(51) Int. Cl.

| | |
|---|---|
| *G06T 11/60* | (2006.01) |
| *G16H 30/40* | (2018.01) |
| *H04N 7/01* | (2006.01) |
| *H04N 7/08* | (2006.01) |

(52) U.S. Cl.
CPC ................ *H04N 7/01* (2013.01); *H04N 7/08*
(2013.01); *G06T 2210/41* (2013.01)

(56) References Cited

U.S. PATENT DOCUMENTS

| | | | |
|---|---|---|---|
| 2021/0200804 A1 | 7/2021 | Barral et al. | |
| 2021/0307841 A1 | 10/2021 | Buch et al. | |
| 2022/0370138 A1* | 11/2022 | Shelton, IV | ........... A61B 34/25 |

* cited by examiner

900

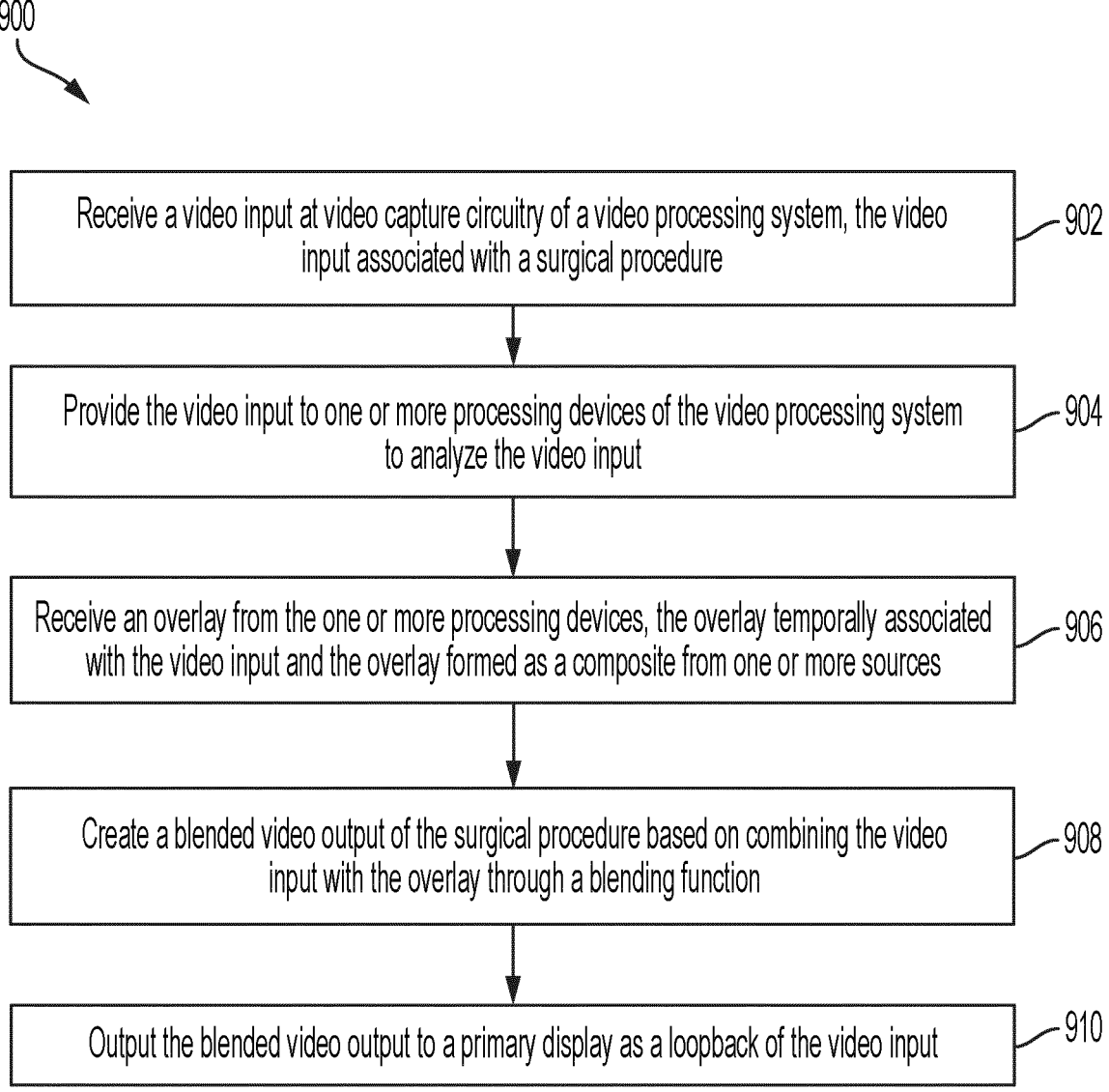

Receive a video input at video capture circuitry of a video processing system, the video input associated with a surgical procedure — 902

Provide the video input to one or more processing devices of the video processing system to analyze the video input — 904

Receive an overlay from the one or more processing devices, the overlay temporally associated with the video input and the overlay formed as a composite from one or more sources — 906

Create a blended video output of the surgical procedure based on combining the video input with the overlay through a blending function — 908

Output the blended video output to a primary display as a loopback of the video input — 910

FIG. 9

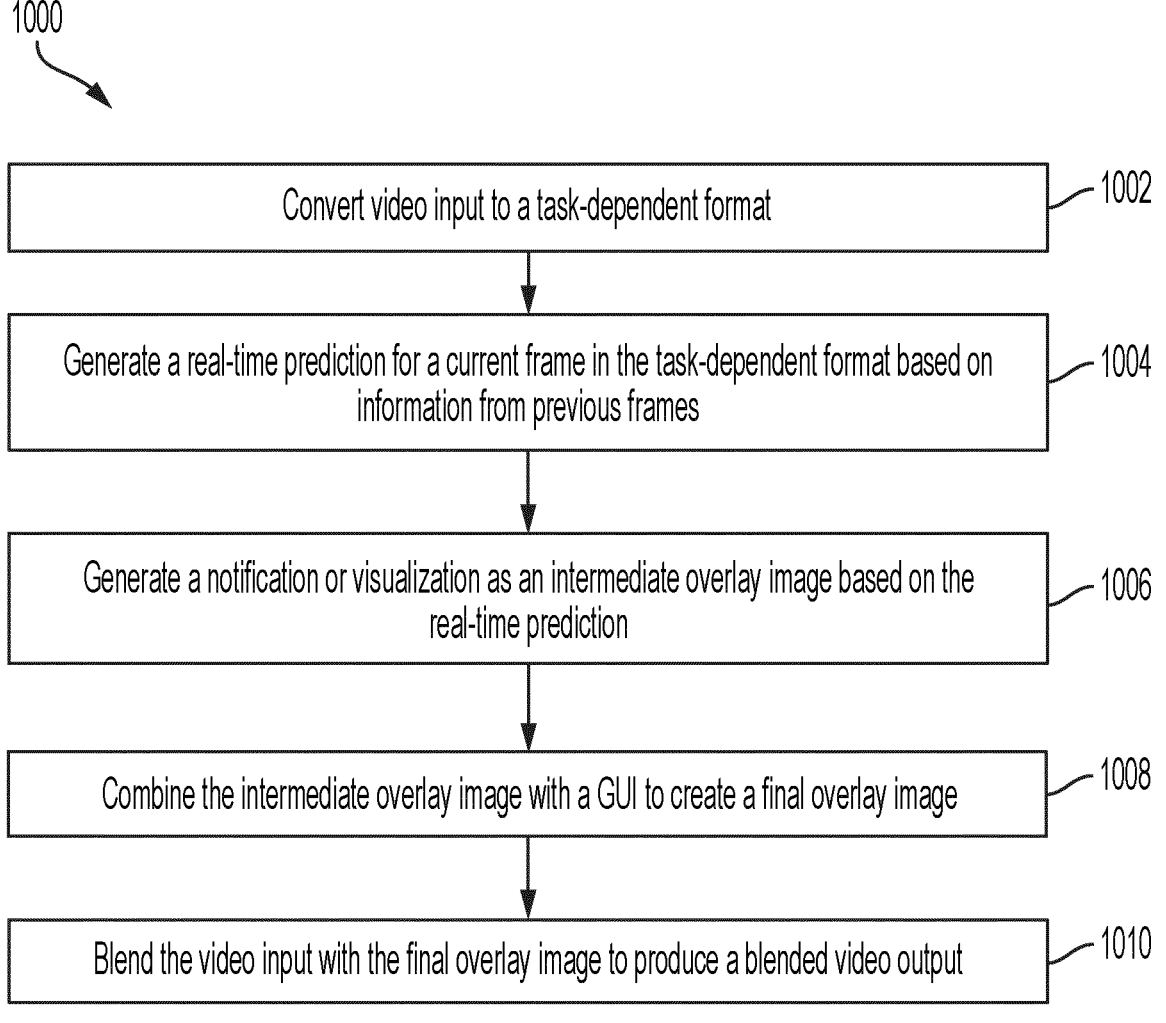

1000

| | |
|---|---|
| Convert video input to a task-dependent format | 1002 |
| Generate a real-time prediction for a current frame in the task-dependent format based on information from previous frames | 1004 |
| Generate a notification or visualization as an intermediate overlay image based on the real-time prediction | 1006 |
| Combine the intermediate overlay image with a GUI to create a final overlay image | 1008 |
| Blend the video input with the final overlay image to produce a blended video output | 1010 |

FIG. 10

LOW-LATENCY VIDEO CAPTURE AND OVERLAY

CROSS REFERENCE TO RELATED APPLICATIONS

This application is a National Stage application of PCT/EP2022/079440, filed Oct. 21, 2022, which claims the benefit of GR application No. 20210100720, filed on Oct. 21, 2021, both of which are incorporated by reference in their entirety herein.

BACKGROUND

The present invention relates in general to computing technology and relates more particularly to computing technology for providing low-latency video capture and overlay.

In time-sensitive video processing environments, delays in processing of video signals can be distracting to users performing real-time procedures that rely upon the video. For example, in a surgical environment, a surgeon using video from one or more cameras may view the video on a display to make decisions and take actions during a surgical procedure based on the video and information visible on the display. Perceivable delays in the displayed video and information can make the surgical procedure more challenging for the surgeon and supporting medical staff.

SUMMARY

According to an aspect, a computer-implemented method includes receiving a video input at video capture circuitry of a video processing system, where the video input is associated with a surgical procedure. The video input is provided to one or more processing devices of the video processing system to analyze the video input. An overlay from the one or more processing devices is received, where the overlay is temporally associated with the video input, and the overlay is formed as a composite from one or more sources. A blended video output of the surgical procedure is created based on combining the video input with the overlay through a blending function. The blended video output is output to a primary display as a loopback of the video input.

According to another aspect, a video processing system includes one or more processing devices, a primary display interface, and video capture circuitry. The video capture circuitry is configured to receive a video input associated with a surgical procedure, provide the video input to the one or more processing devices to analyze the video input, receive an overlay from the one or more processing devices, create a blended video output of the surgical procedure based on combining the video input with the overlay, and output the blended video output to a primary display through the primary display interface as a loopback of the video input.

According to another aspect, a computer program product includes a device having executable instructions stored thereon, which when executed by a video processing system cause the video processing system to perform a method. The method includes receiving a video input associated with a surgical procedure at video capture circuitry of the video processing system and receiving an overlay from one or more processing devices of the video processing system, where the overlay is temporally associated with the video input. A blended video output of the surgical procedure is created as a loopback of the video input based on combining the video input with the overlay. The blended video output is output to a primary display, where the video processing system interfaces with a secondary display, and a primary display output of the video processing system has a lower latency than a secondary display output of the video processing system.

Additional technical features and benefits are realized through the techniques of the present invention. Aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the invention are apparent from the following detailed description taken in conjunction with the accompanying drawings in which:

FIG. 9 depicts a flowchart of a method for providing low-latency video capture and overlay according to one or more aspects; and FIG. 10 depicts a flowchart of a method for providing low-latency video capture and overlay according to one or more aspects.

The diagrams depicted herein are illustrative. There can be many variations to the diagram or the operations described therein without departing from the spirit of the invention. For instance, the actions can be performed in a differing order, or actions can be added, deleted, or modified. Also, the term "coupled" and variations thereof describe having a communications path between two elements and do not imply a direct connection between the elements with no intervening elements/connections between them. All of these variations are considered a part of the specification.

DETAILED DESCRIPTION

In exemplary aspects of the technical solutions described herein, a computer-assisted surgical (CAS) system is provided that supports real-time acquisition and use of multiple sources in real-time. The CAS system can integrate the use of instruments and devices that generate and/or receive video or other types of data during a medical procedure. Some instruments, sensors, cameras, and robotic surgery systems, for example, may have various communication interface options available. For instance, some data/video sources may use coaxial cables, High-Definition Multimedia Interface (HDMI) cables, Ethernet cables, DisplayPort cables, Universal Serial Bus (USB) connectors, optical links, proprietary connections, and other such communication interfaces. A CAS system can include multiple computing devices to provide user interfaces, video displays, and provide enhanced features customized to the surgical procedure being performed, for instance, through computer vision, machine learning, artificial intelligence (AI), and other such supporting technologies.

In some CAS systems, surgeons and/or medical staff may rely upon video data in real-time to perform surgical procedures. Video data and other surgical data may also be captured to support later analysis and/or for training purposes. Video can be used to observe one or more angles of a surgical procedure, which may be captured using an endoscopic camera passed inside a patient adjacent to the location of the surgical procedure to view and record one or more actions performed during the surgical procedure, for example. The video that is captured can be transmitted and/or recorded in one or more examples. In some examples, portions of the video can be analyzed and annotated post-surgery. Data gathered from various surgical instruments can also be processed for real-time use during the surgical procedure and/or recording for later use. A technical challenge exists in processing video of a surgical procedure with minimal latency as the surgical procedure is performed using a CAS system. Exemplary aspects of technical solutions described herein relate to, among other things, devices, systems, methods, computer-readable media, techniques, and methodologies for providing low-latency video capture and the addition of overlays in a surgical environment.

Figure 1:
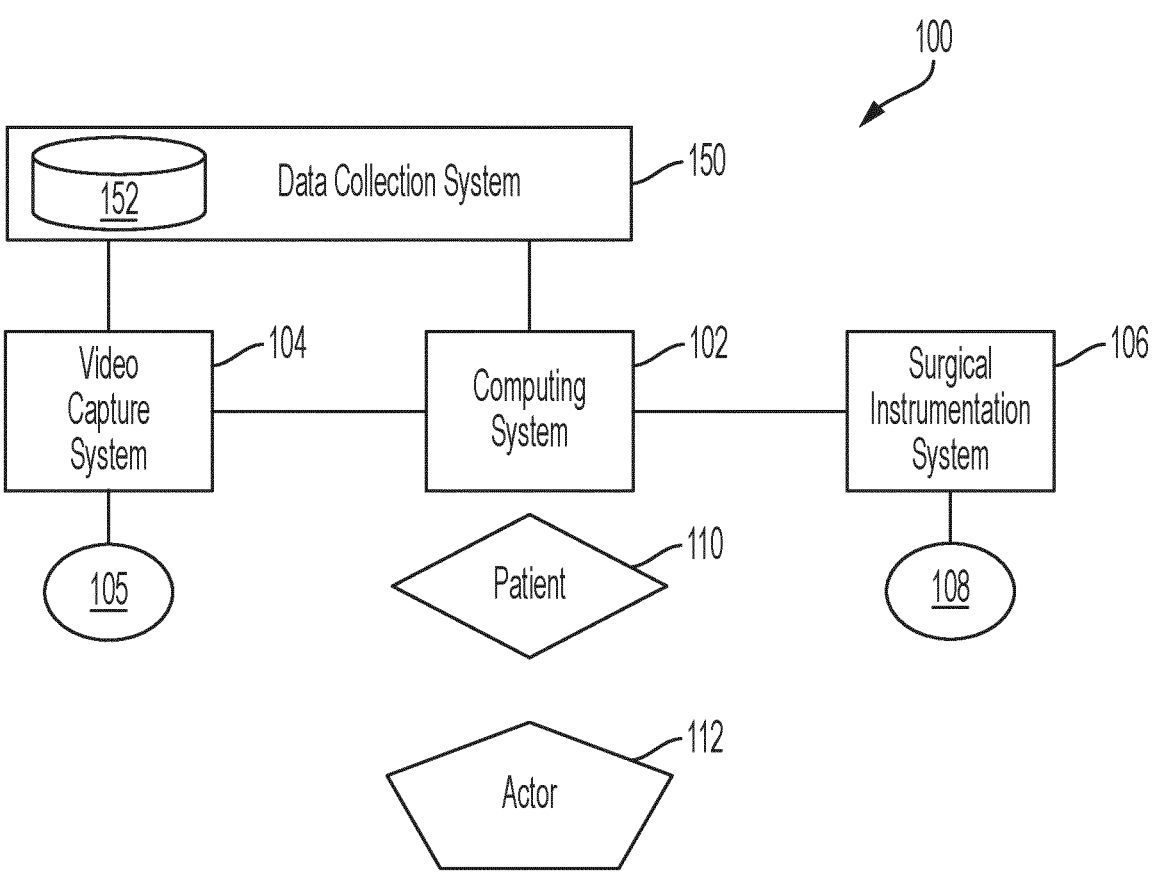
FIG. 1 depicts a computer-assisted surgery system in a surgical environment according to one or more aspects.

FIG. 1 depicts an example CAS system according to one or more aspects. The CAS system 100 includes at least a computing system 102, a video capture system 104, and a surgical instrumentation system 106. As illustrated in FIG. 1, an actor 112 can be medical personnel that uses the CAS system 100 to perform a surgical procedure on a patient 110. Medical personnel can be a surgeon, assistant, nurse, administrator, or any other actor that interacts with the CAS system 100 in a surgical environment. The surgical procedure can be any type of surgery, such as but not limited to cataract surgery, laparoscopic cholecystectomy, robotic procedures, endoscopic endonasal transsphenoidal approach (eTSA) to resection of pituitary adenomas, or any other surgical procedure. In other examples, actor 112 can be a technician, an administrator, an engineer, or any other such personnel that interacts with the CAS system 100. For example, actor 112 can record data from the CAS system 100, configure/update one or more attributes of the CAS system 100, review past performance of the CAS system 100, repair the CAS system 100, etc.

A surgical procedure can include multiple phases, and each phase can include one or more surgical actions. A "surgical action" can include an incision, a compression, a stapling, a clipping, a suturing, a cauterization, a sealing, or any other such actions performed to complete a phase in the surgical procedure. A "phase" represents a surgical event that is composed of a series of steps (e.g., closure). A "step" refers to the completion of a named surgical objective (e.g., hemostasis). During each step, certain surgical instruments 108 (e.g., forceps) are used to achieve a specific objective by performing one or more surgical actions.

The surgical instrumentation system 106 can provide electrical energy to operate one or more surgical instruments 108 to perform the surgical actions. The electrical energy triggers an activation in the surgical instrument 108. The electrical energy can be provided in the form of an electrical current or an electrical voltage. The activation can cause a surgical action to be performed. The surgical instrumentation system 106 can further include electrical energy sensors, electrical impedance sensors, force sensors, bubble and occlusion sensors, and various other types of sensors. The electrical energy sensors can measure and indicate an amount of electrical energy applied to one or more surgical instruments 108 being used for the surgical procedure. The impedance sensors can indicate an amount of impedance measured by the surgical instruments 108, for example, from the tissue being operated upon. The force sensors can indicate an amount of force being applied by the surgical instruments 108. Measurements from various other sensors, such as position sensors, pressure sensors, flow meters, can also be input.

The video capture system 104 includes one or more cameras 105, such as operating room cameras, endoscopic cameras, etc. The cameras 105 capture video data of the surgical procedure being performed. The cameras 105 can capture video in the visible and/or non-visible spectrum, such as infrared, near infrared, ultraviolet, thermal and/or other spectral ranges. The camera may also be another energy source such as a fluoroscopy system which also generate digital video information. The video capture system 104 includes one or more video capture devices that can include cameras 105 placed in the surgical room to capture events surrounding (i.e., outside) the patient being operated upon. The video capture system 104 further includes cameras 105 that are passed inside (e.g., endoscopic cameras) the patient 110 to capture endoscopic data or can be placed outside in exoscope or microscope configurations. The endoscopic data provides video and images of the surgical procedure.

The computing system 102 includes one or more memory devices, one or more processors, a user interface device, among other components. The computing system 102 can execute one or more computer-executable instructions. The execution of the instructions facilitates the computing system 102 to perform one or more methods, including those described herein. The computing system 102 can communicate with other computing systems via a wired and/or a wireless network. In one or more examples, the computing system 102 includes one or more trained machine learning models that can detect and/or predict features of/from the surgical procedure that is being performed or has been performed earlier. Features can include structures such as anatomical structures, surgical instruments 108 in the captured video of the surgical procedure. Features can further include events such as phases, actions in the surgical procedure. Features that are detected can further include the actor 112 and/or patient 110. Based on the detection, the computing system 102, in one or more examples, can provide recommendations for subsequent actions to be taken by the actor 112. Alternatively, or in addition, the computing system 102 can provide one or more reports based on the detections. The detections by the machine learning models can be performed in an autonomous or semi-autonomous manner.

The machine learning models can include artificial neural networks, such as deep neural networks, convolutional neural networks, recurrent neural networks, encoders, decoders, or any other type of machine learning model. The machine learning models can be trained in a supervised, unsupervised, or hybrid manner. The machine learning models can be trained to perform detection and/or prediction using one or more types of data acquired by the CAS system 100. For example, the machine learning models can use the video data captured via the video capture system 104. Alternatively, or in addition, the machine learning models use the surgical instrumentation data from the surgical instrumentation system 106. In yet other examples, the machine learning models use a combination of video data and surgical instrumentation data.

In one or more examples, the machine learning models can detect surgical actions, surgical phases, anatomical structures, surgical instruments, and various other features from the data associated with a surgical procedure. Features can also be sourced from systems that manage electronic medical records for patients and/or scheduling systems associated with scheduling of surgical procedures. The features can be used to group aspects for machine learning based on various criteria, such as patient characteristics, facilities used, planned procedure duration, and other such parameters. The detection can be performed in real-time in some examples. Alternatively, or in addition, the computing system 102 analyzes the surgical data, i.e., the various types of data captured during the surgical procedure, in an offline manner (e.g., post-surgery). In one or more examples, the machine learning models detect surgical phases based on detecting some of the features such as the anatomical structure, surgical instruments, etc.

A data collection system 150 can be employed to store the surgical data, including the video(s) captured during the surgical procedures. The data collection system 150 includes one or more storage devices 152. The data collection system 150 can be a local storage system, a cloud-based storage system, or a combination thereof. Further, the data collection system 150 can use any type of cloud-based storage architecture, for example, public cloud, private cloud, hybrid cloud, etc. In some examples, the data collection system can use a distributed storage, i.e., the storage devices 152 are located at different geographic locations. The storage devices 152 can include any type of electronic data storage media used for recording machine-readable data, such as semiconductor-based, magnetic-based, optical-based storage media, or a combination thereof. For example, the data storage media can include flash-based solid-state drives (SSDs), magnetic-based hard disk drives, magnetic tape, optical discs, etc.

In one or more examples, the data collection system 150 can be part of the video capture system 104, or vice-versa. In some examples, the data collection system 150, the video capture system 104, and the computing system 102, can communicate with each other via a communication network, which can be wired, wireless, or a combination thereof. The communication between the systems can include the transfer of data (e.g., video data, instrumentation data, etc.), data manipulation commands (e.g., browse, copy, paste, move, delete, create, compress, etc.), data manipulation results, etc. In one or more examples, the computing system 102 can manipulate the data already stored/being stored in the data collection system 150 based on outputs from the one or more machine learning models, e.g., phase detection, structure detection, etc. Alternatively, or in addition, the computing system 102 can manipulate the data already stored/being stored in the data collection system 150 based on information from the surgical instrumentation system 106.

Figure 2:
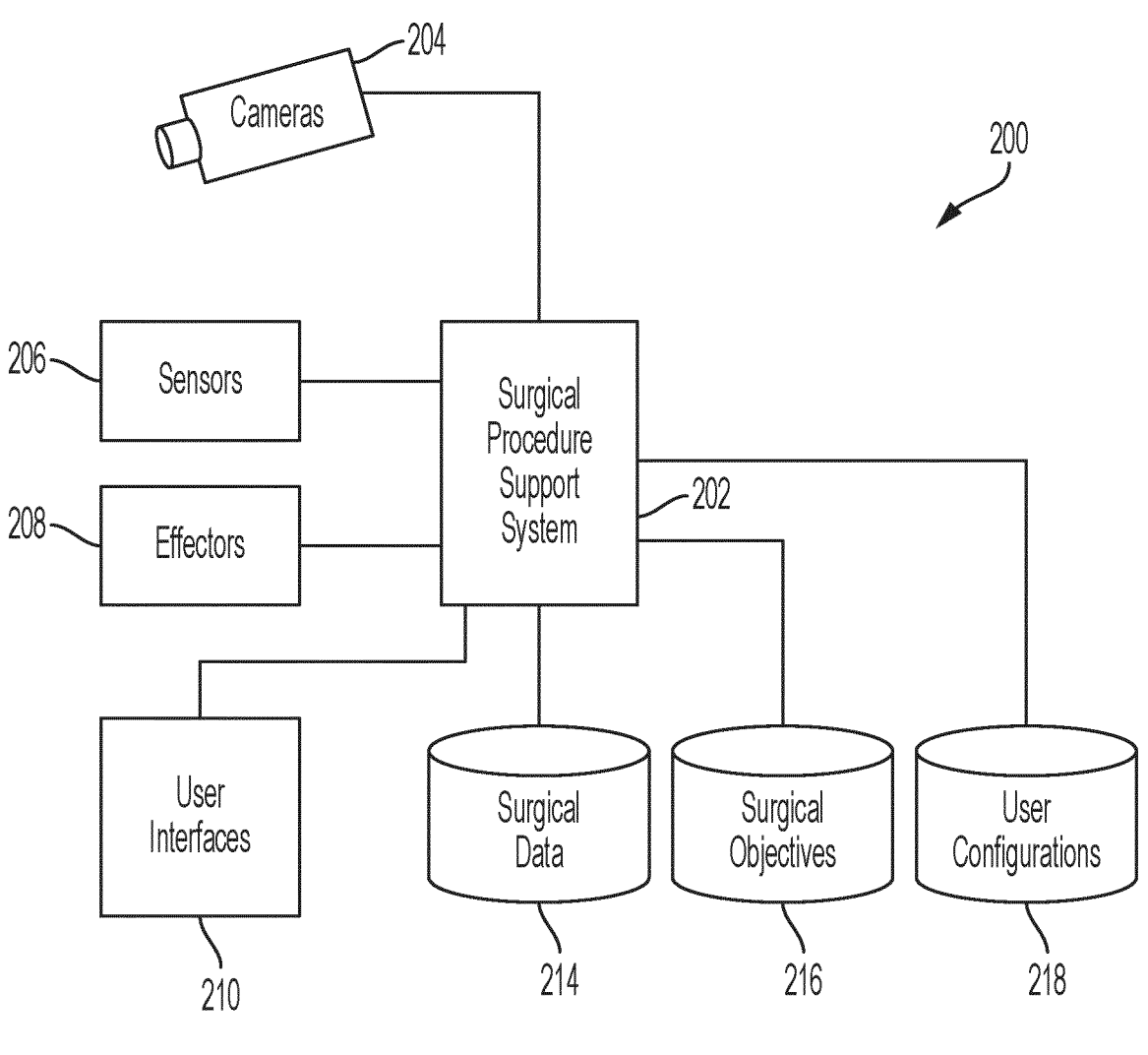
FIG. 2 depicts a surgical procedure system according to one or more aspects.

FIG. 2 depicts a surgical procedure system 200 in accordance with one or more aspects. The example of FIG. 2 depicts a surgical procedure support system 202 that can include or may be coupled to the system 100 of FIG. 1. The surgical procedure support system 202 can acquire image or video data using one or more cameras 204. The surgical procedure support system 202 can also interface with a plurality of sensors 206 and effectors 208. The sensors 206 may be associated with surgical support equipment and/or patient monitoring. The effectors 208 can be robotic components or other equipment controllable through the surgical procedure support system 202. The surgical procedure support system 202 can also interact with one or more user interfaces 210, such as various input and/or output devices. The surgical procedure support system 202 can store, access, and/or update surgical data 214 associated with a training dataset and/or live data as a surgical procedure is being performed on patient 110 of FIG. 1. The surgical procedure support system 202 can store, access, and/or update surgical objectives 216 to assist in training and guidance for one or more surgical procedures. User configurations 218 can track and store user preferences.

When implemented using the configuration of system 200 of FIG. 2, for example, the cameras 204 are an example of the video sources that may be wired or wirelessly linked to the surgical procedure support system 202. Sensors 206 are an example of data sources that can be wired or wirelessly linked to the surgical procedure support system 202. Effectors 208 are another example of devices that can be wired or wirelessly linked to the surgical procedure support system 202. The user interfaces 210 can be displayed on one or more of the display devices and can be customized according to the user configurations 218. The surgical data 214 and surgical objectives 216 can be stored and accessed, for example, as part of the video sources and/or data sources.

Figure 3:
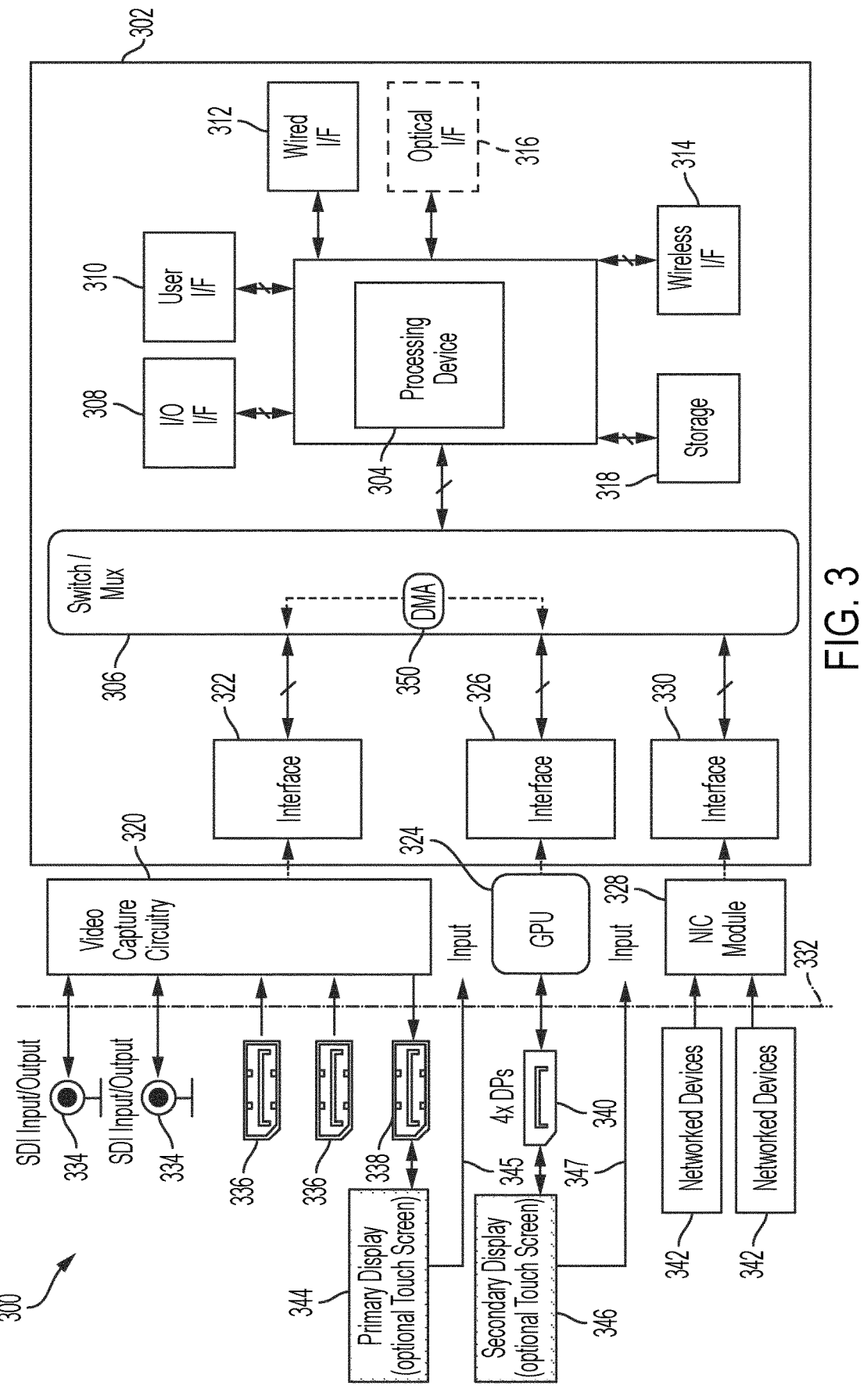
FIG. 3 depicts a video processing system according to one or more aspects.

FIG. 3 depicts a video processing system 300 according to one or more aspects. Various components of the system 100 of FIG. 1 can be integrated together to reduce processing latency and provide flexibility in customizing video and overlays in a surgical procedure. In the example of FIG. 3, the video processing system 300 can incorporate aspects of the computing system 102, the video capture system 104, and the data collection system 150 of FIG. 1. For instance, the video processing system 300 can include a carrier board 302 with a processing device 304, a multiplexing switch 306, and multiple interfaces. The processing device 304 can interface with various inputs and outputs, such as the sensors 206 and effectors 208 of FIG. 2 through an input/output interface 308. User interfaces 310, such as user interfaces 210 of FIG. 2, can be supported the processing device 304 to receive input from various sources, such as buttons, knobs, switches, touchscreen input, and the like. The user interfaces 310 may also support various status indicators and provide general information to one or more users, such as actors 112 of FIG. 1. The processing device 304 can support various communication interfaces through a wired interface 312, a wireless interface 314, and/or an optical interface 316. The wired interface 312 may support various digital and/or analog connections, such as connections using coaxial cables, high-definition multimedia interface (HDMI) cables, Ethernet cables, DisplayPort cables, universal serial bus (USB) connectors, and the like. The wireless interface 314 may include a Wi-Fi chip that supports specific radio frequency transmissions with various security features. Local storage 318 can also be provided at the video processing system 300, which may be integrated with the carrier board 302 and/or include the use of removable storage (e.g., a memory card).

Although one processing device 304 is depicted, it will be understood that the video processing system 300 can include one or more processing devices, which may include one or more processing circuits or cores configured to execute instructions. For instance, the processing device 304 can be a microcontroller, a field programmable gate array, an application specific integrated circuit, a digital signal processor, a graphics processing unit, or other such device capable of executing instructions. The instructions may be stored in memory or embodied in a circuitry configuration of the processing device 304. Further, the processing device 304 can include one or more graphics processing units in combination with one or more processors of various types.

The multiplexing switch 306 can provide expansion capabilities and further configurability of the video processing system 300. In the example of FIG. 3, the multiplexing switch 306 can provide connection paths between the processing device 304 and video capture circuitry 320 through an interface 322. The multiplexing switch 306 can also provide connection paths to a graphics processing unit 324 as another processing device through interface 326 and to a network interface controller module 328 through interface 330. The multiplexing switch 306 may also have spare capacity for further expansion capability. The interfaces 322, 326, and 330 can support various bus formats, such as Peripheral Component Interconnect Express (PCIe) or other bus technologies.

The video capture circuitry 320, graphics processing unit 324, and network interface controller module 328 can be pluggable cards or modules that process video and/or network data through an external boundary 332 of the video processing system 300. For example, the video capture circuitry 320 can interface with multiple serial digital interface (SDI) ports 334 as one type of digital video input/output. The video capture circuitry 320 can also interface with one or more ports 336 and ports 338. In some aspects, ports 336 and 338 may be configured for unidirectional operation. For instance, ports 336 may be configured as one or more input ports and ports 338 may be configured as one or more output ports. Ports 336 and 338 can be any supported video port type, such as HDMI, digital visual interface (DVI), DisplayPort, and/or other display interface type known in the art. The graphics processing unit 324 can interface with one or more display ports 340 (e.g., ports that comply with DisplayPort standards). The network interface controller module 328 can interface with one or more networked devices 342. The networked devices 342 can include various devices and system components of the CAS system 100 of FIG. 1 that can provide surgical data or may be configured to receive video and/or other such data from the video processing system 300. The network interface controller module 328 can further expand the networking capability of the video processing system 300 to a greater number of communication channels beyond those already supported through the wired interface 312, wireless interface 314, and/or optical interface 316.

The port 338 may also be referred to as a primary display output 338 of the video processing system 300, and one or more of the display ports 340 may also be referred to as a secondary display output 340 of the video processing system 300. The primary display output 338 can interface with a primary display 344, and the secondary display output 340 can interface with a secondary display 346. The primary display 344 may be implemented as a touch screen, where input 345 received through the primary display 344 can be sent to the user interface 310. Similarly, the secondary display 346 can be implemented as a touch screen, where input 347 from the secondary display 346 can be sent to the user interface 310. The primary display 344 may be used directly by a surgeon during a surgical procedure, and thus, the primary display output 338 can be implemented as a low/near-zero latency output to the primary display 344. Low/near-zero latency can be defined, for example, as a latency of half of a video line or less for video input provided in a loopback to the primary display output 338 and an overlay selectively added to the video input in the loopback. The loopback refers to the near immediate return of a video input to a video output, such as video input received through a camera 105, 204 via one or more from ports 334, 336 for the primary display output 338. For example, the latency can be on the order of microseconds to milliseconds. The secondary display 346 may not be used directly by the surgeon during a surgical procedure, and thus, the secondary display output 340 to the secondary display 346 need not have as low latency as the video processing path through the video capture circuitry 320 to the primary display 344. As an example, the secondary display 346 may be an auxiliary output used to monitor surgical procedure status, vital signs, instrument data, and various video feeds by medical staff. A portion of the information output to the secondary display 346 may be of interest to the surgeon while performing the surgical procedure. As such, a portion of the information output to the secondary display 346 may be provided as an overlay in a blended video output to the primary display 344.

To support video feed routing between the video capture circuitry 320, graphics processing unit 324, network interface controller module 328, and/or processing device 304, the multiplexing switch 306 can include a direct memory access controller 350. For instance, the direct memory access controller 350 can be configured to provide video input from the video capture circuitry 320 to one or more processing devices, such as processing device 304 and/or graphics processing unit 324. The processing device 304 and/or graphics processing unit 324 can configure the direct memory access controller 350 to send data or video information to be blended as an overlay to the video capture circuitry 320 for output to the primary display 344. For instance, the video capture circuitry 320, graphics processing unit 324, network interface controller module 328, and/or processing device 304 may each have internal buffers that are addressable by the direct memory access controller 350 such that data or video content can be stored or retrieved by the direct memory access controller 350 to facilitate movement through the various components of the video processing system 300. The direct memory access controller 350 can be a remote direct memory access controller and may be implemented in various locations within the video processing system 300. The direct memory access controller 350 can support various bus protocols for data transfer without processor intervention. When implemented as a remote direct memory access controller, the direct memory access controller 350 may support various network communication protocols for data transfer without processing intervention. Although a single instance of the direct memory access controller 350 is depicted, there can be multiple instances of the direct memory access controller 350 to support multiple communication channels in parallel, which can include a mix of bus protocols and/or network protocols. Data exchange between the components of the video processing system 300 can also be performed using other communication/bus protocols.

Additionally, exemplary aspects of technical solutions described herein relate to, among other things, devices, systems, methods, computer-readable media, techniques, and methodologies for using machine learning and computer vision to automatically predict or detect surgical phases and instruments in surgical data. More generally, aspects can include detection, tracking, and predictions associated with one or more structures, the structures being deemed to be critical for an actor involved in performing one or more actions during a surgical procedure (e.g., by a surgeon).

Prediction, tracking and/or detection processing can be distributed between multiple processing components, such as the processing device 304, the graphics processing unit 324, surgical procedure support system 202 of FIG. 2 and/or components of the CAS system 100 of FIG. 1. In one or more aspects, the structures are predicted dynamically and substantially in real-time as the surgical data, including the video, is being captured and analyzed by technical solutions described herein. A predicted structure can be an anatomical structure, a surgical instrument, etc.

The surgical data provided to train the machine learning models can include data captured during a surgical procedure and simulated data. The surgical data can include time-varying image data (e.g., a simulated/real video stream from different types of cameras) corresponding to a surgical environment. The surgical data can also include other types of data streams, such as audio, radio frequency identifier (RFID), text, robotic sensors, other signals, etc. The machine learning models are trained to predict and identify, in the surgical data, "structures," including particular tools, ana-tomic objects, actions being performed in the simulated/real surgical stages. In one or more aspects, the machine learning models are trained to define one or more models' parameters to learn how to transform new input data (that the models are not trained on) to identify one or more structures. During the training, the models receive, as input, one or more data streams that may be augmented with data indicating the structures in the data streams, such as indicated by metadata and/or image-segmentation data associated with the input data. The data used during training can also include temporal sequences of one or more input data.

The machine learning models, once trained, can analyze the input surgical data, and in one or more aspects, predict and/or characterize structures included in the video data included with the surgical data. The video data can include sequential images and/or encoded video data (e.g., using digital video file/stream formats and/or codecs, such as MP4, MOV, AVI, WEBM, AVCHD, OGG, etc.). The pre-diction and/or characterization of the structures can include segmenting the video data or predicting the localization of the structures with a probabilistic heatmap. In some instances, the one or more machine learning models include or are associated with a preprocessing or augmentation (e.g., intensity normalization, resizing, cropping, etc.) that is per-formed prior to segmenting the video data. An output of the one or more machine learning models can include image-segmentation or probabilistic heatmap data that indicates which (if any) of a defined set of structures are predicted within the video data, a location and/or position and/or pose of the structure(s) within the video data, and/or state of the structure(s). The location can be a set of coordinates in an image/frame in the video data. For example, the coordinates can provide a bounding box. The coordinates can provide boundaries that surround the structure(s) being predicted. The machine learning models, in one or more examples, are trained to perform higher-level predictions and tracking, such as predicting a phase of a surgical procedure and tracking one or more surgical instruments used in the surgical procedure.

Figure 4:
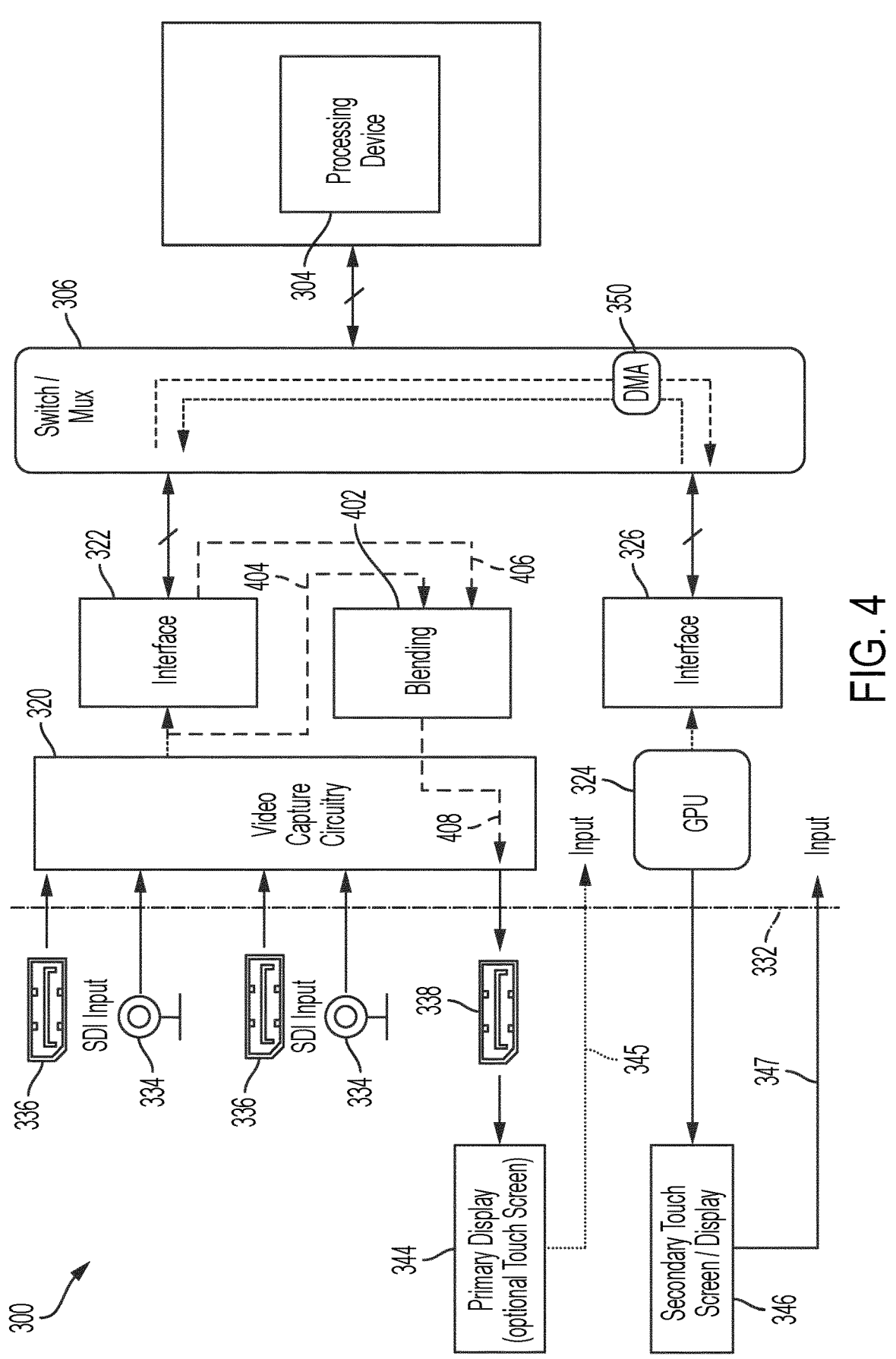
FIG. 4 depicts a portion of the video processing system of FIG. 3 with further detail according to one or more aspects.

Various outputs of machine learning and other associated data sources can be combined with video input as an overlay in a blended video output. A blending function 402 is depicted in the example of FIG. 4 that depicts a portion of the video processing system 300 of FIG. 3 with further detail. The blending function 402 can receive video input 404 from the video capture circuitry 320 and an overlay 406 from one or more processing devices, such as processing device 304 and/or graphics processing unit 324, and creates a blended video output 408 of a surgical procedure based on combining the video input 404 with the overlay 406. The blending can be a direct addition, where the overlay 406 masks content of the video input 404 at selected locations. Further, the blending function 402 may have an adjustable intensity such that otherwise hidden portions of the video input 404 may appear in the background depending upon the intensity setting of the overlay 406. The blending function 402 can be implemented within the video capture circuitry 320 or external to the video capture circuitry 320, such as in supporting circuitry on the carrier board 302. Implementing the blending function 402 in hardware rather than software can reduce latency.

The direct memory access controller 350 can be config-ured to send the overlay 406 to a buffer that continually feeds the blending function 402. The update rate of the overlay 406 may differ from the frame rate of the video input 404. For example, the video input 404 may have a frame rate of 60 Hz, while the overlay 406 may be updated at a lower frequency, such as 12 Hz. In this example, a same copy of the overlay 406 may be used for five consecutive frames of the video input 404. The lower update rate of the overlay 406 can allow for additional processing time while keeping the blended video output 408 to the primary display 344 oper-ating at 60 Hz in this example. This can provide a reduced/ near-zero latency in the perception of the underlying video as observed by the used of the primary display 344. The overlay 406 provides additional information that may not be changing rapidly. Further, if a source of the overlay 406 has a fault or another type of error condition occurs, the user of the primary display 344 can turn-off/deactivate the overlay 406 without a noticeable impact to the video quality and latency of the blended video output 408 to the primary display 344. Although one example of a rate difference is described in this example, many ratios can be supported between the update rate of the video input 404 and the overlay 406, including a one-to-one ratio. The overlay 406 can be a composite of multiple overlays from different sources, such as a visualization or notification generated by a model, status information, a menu, a toolbar, a message, and/or other such information. In some aspects, a single source can combine multiple features to form a composite for overlay.

As one example, a portion of the output of the graphics processing unit 324 that is output to the secondary display 346 can be routed through the multiplexing switch 306 using, for instance, the direct memory access controller 350 as a portion of the overlay 406 such that the user of the primary display 344 can view at least a portion of the output to the secondary display 346. The user of the primary display 344 may be able to turn blending of the overlay 406 on or off and configure aspects, such as desired content and positioning of the overlay 406 in the blended video output 408. Selections made through the secondary display 346 do not impact the primary display 344.

Figure 5:
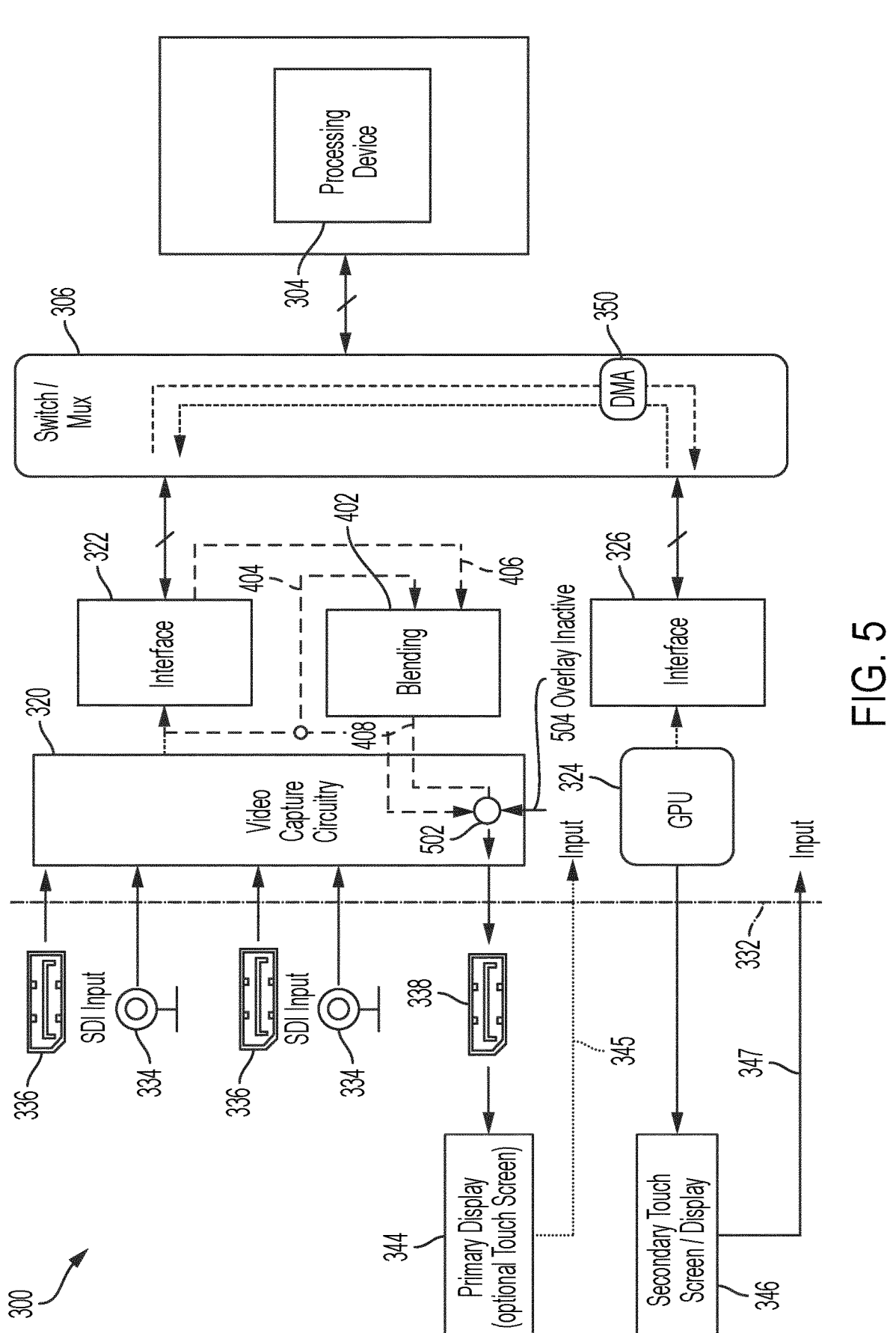
FIG. 5 depicts an alternate configuration of the video processing system of FIG. 4 according to one or more aspects.

FIG. 5 depicts a block diagram of an alternate configu-ration of the video processing system 300 of FIGS. 3 and 4. In the example of FIG. 5, a bypass function 502 can be incorporated in the video capture circuitry 320. The bypass function 502 can bypass the blending function 402 to route the video input 404 directly to the primary display 344 based on determining that the overlay 406 is inactive or an error condition exists. For example, an overlay inactive 504 state can be set based on detecting that no content has been provided as the overlay 406. Further, the overlay inactive 504 state may be set based on a request of the user of the primary display 344. The use of the bypass 502 may further reduce latency by avoiding any delays associated with passing the video input 404 through the blending function 402. The loopback of the video input 404 can also be provided without the overlay 406 where various types of error conditions are detected. For example, a software crash or power fault in another component of the system 300 can set the overlay inactive 504 state to maintain video loopback as long as the video capture circuitry 320 remains powered. The content of the overlay 406 can also be monitored to detect an error condition, such as a signal loss, an opaque black frame as an overlay, and other irregularities or input errors such that distortion of the video loopback is avoided through the blending function 402. The video capture circuitry 320 can also include various integrity checks to detect errors introduced in the transmission of data from other components of the system 300 to set the overlay inactive 504 state. Data integrity can be based on various aspects, such as bit errors, noise detection, synchronization/timing detection, loss detection, protocol errors, and other such checks for errors or distortion. In some aspects, the overlay inactive 504 state can be set by a watchdog function based on an absence of input or activity over a predetermined period of time.

Figure 6:
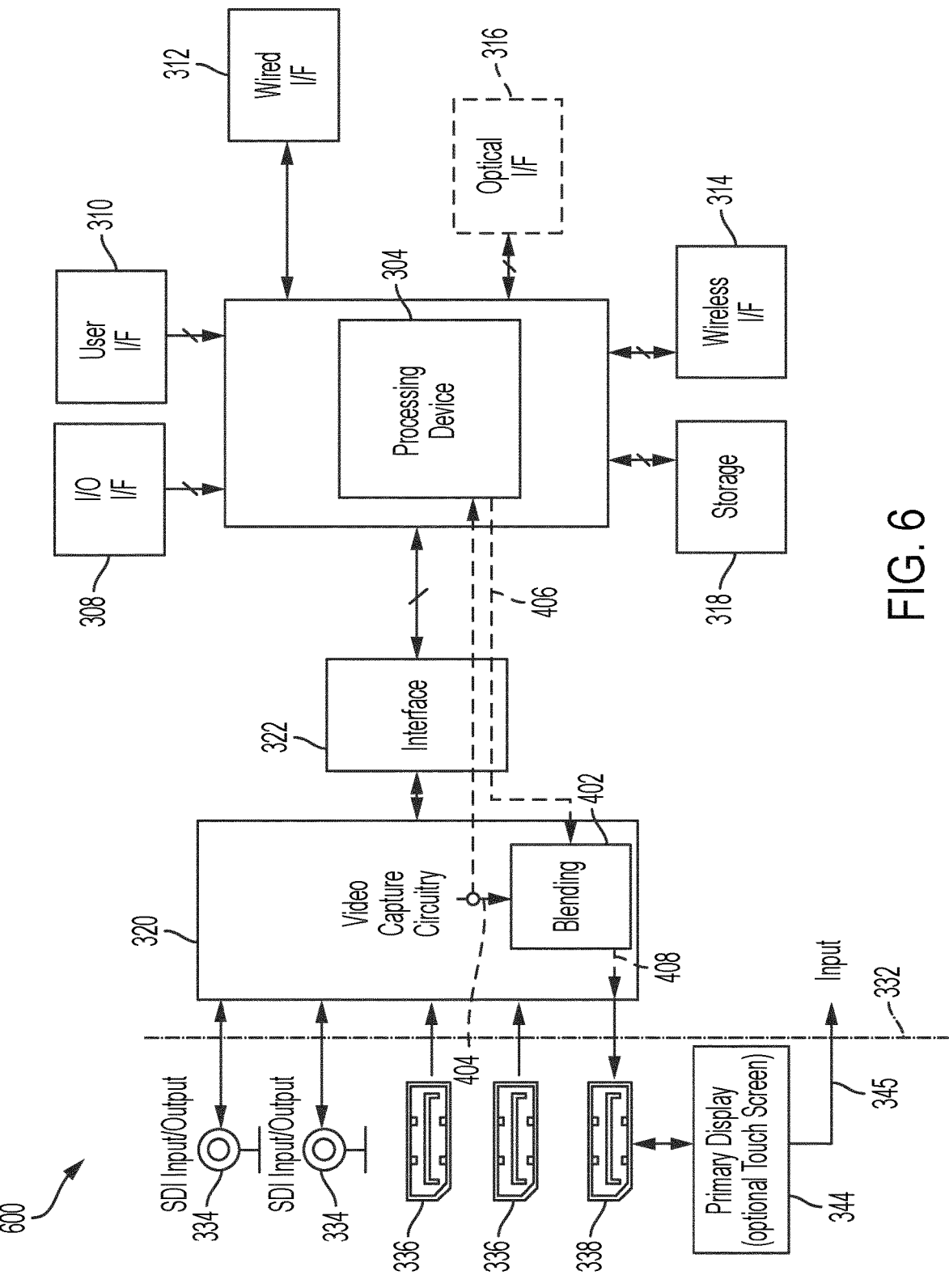
FIG. 6 depicts a video processing system according to one or more aspects.

FIG. 6 depicts a video processing system 600 according to one or more aspects as a reduced functionality version of the video processing system 300 of FIGS. 3-5. In the example of FIG. 6, the video processing system 600 interfaces with the primary display 344 but excludes the graphics processing unit 324 and network interface controller module 328 of FIG. 3. As such, the multiplexing switch 306 can also be omitted in the video processing system 600, and the video capture circuitry 320 can communicate with the processing device 304 through interface 322. According to some aspects, a reduced version of the multiplexing switch 306 can be implemented in the video processing system 600, for example, to provide a path to the storage 318 or other interfaces of the video processing system 600.

Further, FIG. 6 also illustrates an example of the blending function 402 being implemented within the video capture circuitry 320. In this example, the video input 404 can be provided to the processing device 304, and the processing device 304 can provide the overlay 406 to the blending function 402 to create a blended video output 408 of a surgical procedure based on combining the video input 404 with the overlay 406.

Figure 7:
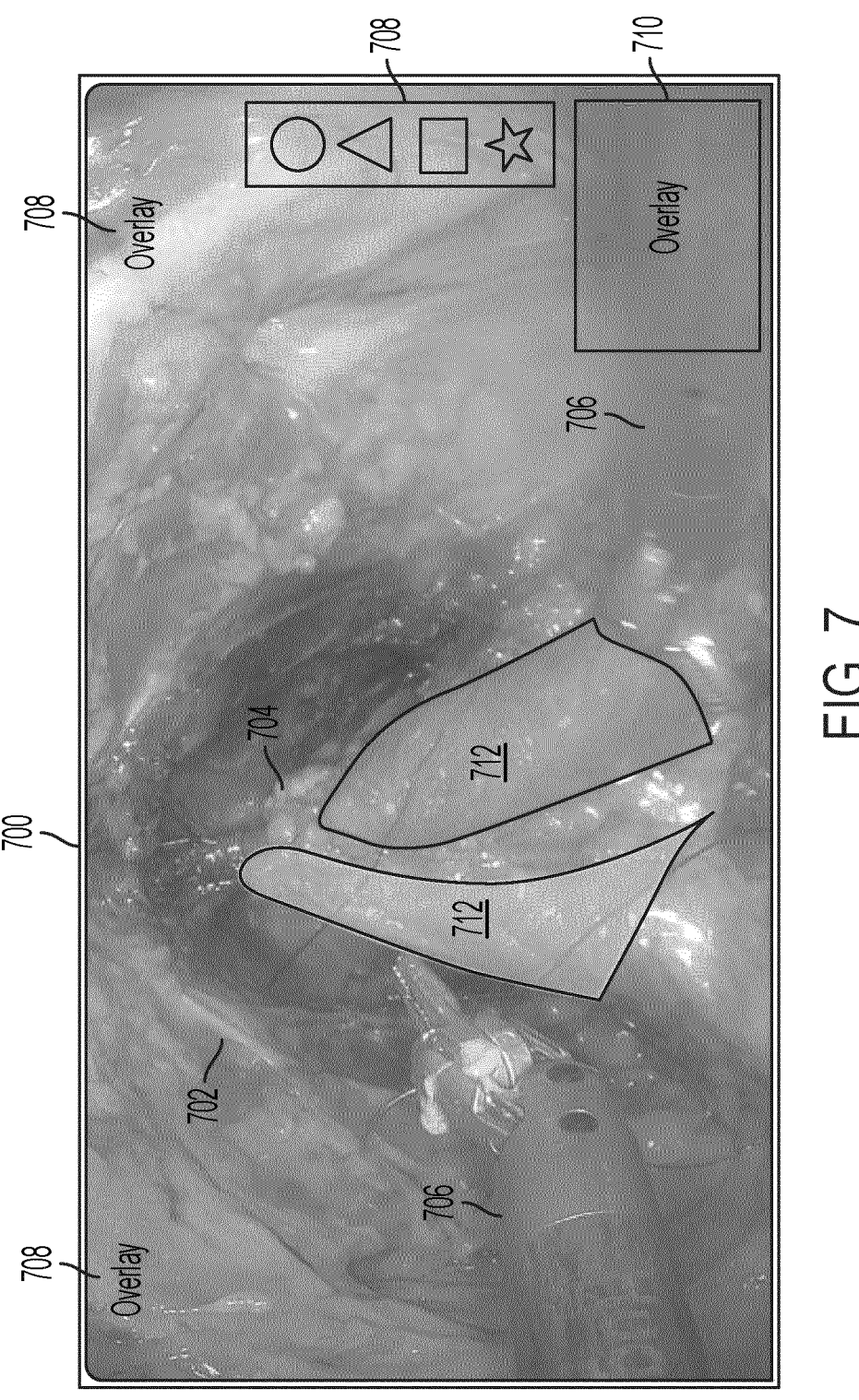
FIG. 7 depicts an example of a video with overlays according to one or more aspects.

FIG. 7 depicts an example of a blended video output 700 with overlays according to one or more aspects. The blended video output 700 can include video input 702 as captured by a camera, such as cameras 105, 204 of FIGS. 1 and 2. The blended video output 700 can depict critical structures 704 and surgical tools 706 used in a surgical procedure. Various types of overlays 708, 710, 712 can be added to the video input 702 in creating the blended video output 700. For example, overlays 708 can include procedure information associated with the current scene. Overlay 710 can be a picture-in-picture type display that includes at least a portion of an auxiliary output provided to a secondary display 346 of FIGS. 3-5. Overlays 712 can be based on critical structure detection and/or surgical phase detection associated with the video input 702. The overlays 708, 710, 712 can be generated by the processing device 304 of FIGS. 3-6 and/or graphics processing unit 324 of FIGS. 3-5. The overlays 708, 710, 712 are substantially temporally aligned with the video input 702, although an underlying update rate of the overlays 708, 710, 712 may differ from the video input 702. Further, updates to the overlays 708, 710, 712 can have an extended latency as compared to the video input 702, although the added delay may not be noticeable to users, for example, due to a slower update rate of the overlays 708, 710, 712. The temporal alignment can be a temporal association where the overlays 708, 710, 712 slightly lag the video input 702, which can also result from different processing, filtering, and/or other sources of timing variation.

A compositor function can blend multiple overlays 708, 712 together as a combined overlay from different sources. The compositor function can be part of the blending function 402 or may be implemented separately through one or more upstream sources that blend the overlays 708, 712 together in two or more stages of blending. An overlay that combines multiple overlays, such as overlays 708, 710, and 712, as a composite from one or more sources can be generated in whole or in part by the blending function 402. As an example, overlay 708 can be a graphical user interface (GUI) that includes a menu, toolbar, and/or status information from a first source. Overlay 712 can be generated by AI or a machine learning model as a second source. Thus, overlays 708, 712 may have a relatively low update frequency as compared to the video display update frequency. Where the overlay 710 is a video stream, the overlay 710 may be blended with a combination of one or more of the overlays 708, 712 and the video input 702 to create the blended video output 700. Further, where split screen output is supported, multiple video sources can be blended targeting predetermined display regions to generate the blended video output 700. Thus, the blended video output 700 can be a composite view of multiple sources. Overlays 708, 710, 712 can target different regions of a display or can overlap each other.

Figure 8:
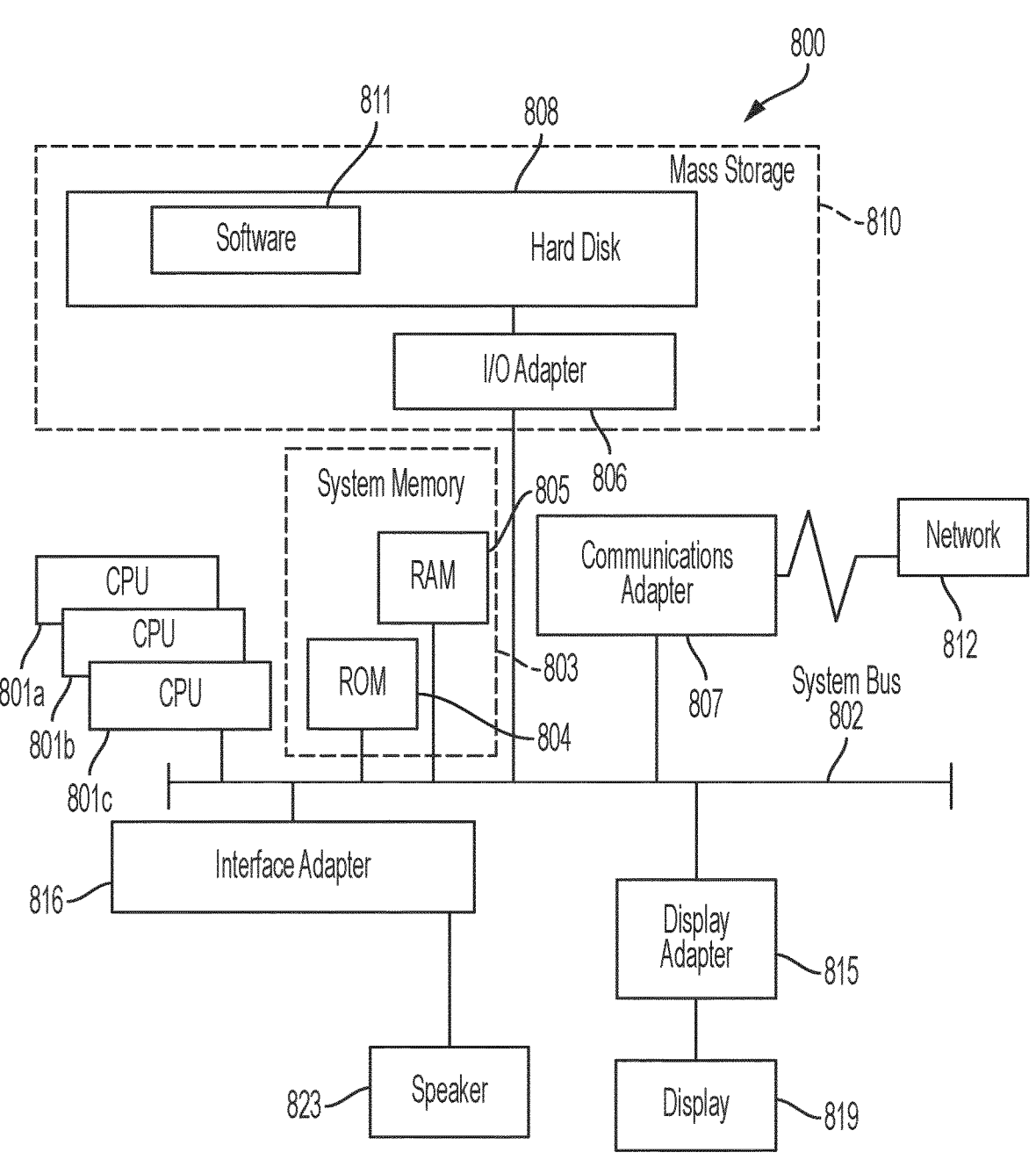
FIG. 8 depicts a computer system in accordance with one or more aspects.

Turning now to FIG. 8, a computer system 800 is generally shown in accordance with an aspect. The computer system 800 or portions thereof can be used in implementing aspects as described herein. The computer system 800 can be an electronic computer framework comprising and/or employing any number and combination of computing devices and networks utilizing various communication technologies, as described herein. The computer system 800 can be easily scalable, extensible, and modular, with the ability to change to different services or reconfigure some features independently of others. The computer system 800 may be, for example, a server, desktop computer, laptop computer, tablet computer, or smartphone. In some examples, computer system 800 may be a cloud computing node. Computer system 800 may be described in the general context of computer-executable instructions, such as program modules, being executed by a computer system. Generally, program modules may include routines, programs, objects, components, logic, data structures, and so on that perform particular tasks or implement particular abstract data types. Computer system 800 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 8, the computer system 800 has one or more central processing units (CPU(s)) 801a, 801b, 801c, etc. (collectively or generically referred to as processor(s) 801). The processors 801 can be a single-core processor, multi-core processor, computing cluster, or any number of other configurations. The processors 801, also referred to as processing circuits, are coupled via a system bus 802 to a system memory 803 and various other components. The system memory 803 can include one or more memory devices, such as read-only memory (ROM) 804 and a random access memory (RAM) 805. The ROM 804 is coupled to the system bus 802 and may include a basic input/output system (BIOS), which controls certain basic functions of the computer system 800. The RAM is read-write memory coupled to the system bus 802 for use by the processors 801. The system memory 803 provides temporary memory space for operations of said instructions during operation. The system memory 803 can include random access memory (RAM), read-only memory, flash memory, or any other suitable memory systems.

The computer system 800 comprises an input/output (I/O) adapter 806 and a communications adapter 807 coupled to the system bus 802. The I/O adapter 806 may be a small computer system interface (SCSI) adapter that communicates with a hard disk 808 and/or any other similar component. The I/O adapter 806 and the hard disk 808 are collectively referred to herein as a mass storage 810.

Software 811 for execution on the computer system 800 may be stored in the mass storage 810. The mass storage 810 is an example of a tangible storage medium readable by the processors 801, where the software 811 is stored as instructions for execution by the processors 801 to cause the computer system 800 to operate, such as is described hereinbelow with respect to the various Figures. Examples of computer program product and the execution of such instruction is discussed herein in more detail. The communications adapter 807 interconnects the system bus 802 with a network 812, which may be an outside network, enabling the computer system 800 to communicate with other such systems. In one aspect, a portion of the system memory 803 and the mass storage 810 collectively store an operating system, which may be any appropriate operating system to coordinate the functions of the various components shown in FIG. 8.

Additional input/output devices are shown as connected to the system bus 802 via a display adapter 815 and an interface adapter 816 and. In one aspect, the adapters 806, 807, 815, and 816 may be connected to one or more I/O buses that are connected to the system bus 802 via an intermediate bus bridge (not shown). A display 819 (e.g., a screen or a display monitor) is connected to the system bus 802 by a display adapter 815, which may include a graphics controller to improve the performance of graphics-intensive applications and a video controller. A keyboard, a mouse, a touchscreen, one or more buttons, a speaker, etc., can be interconnected to the system bus 802 via the interface adapter 816, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 8, the computer system 800 includes processing capability in the form of the processors 801, and, storage capability including the system memory 803 and the mass storage 810, input means such as the buttons, touchscreen, and output capability including the speaker 823 and the display 819.

In some aspects, the communications adapter 807 can transmit data using any suitable interface or protocol, such as the internet small computer system interface, among others. The network 812 may be a cellular network, a radio network, a wide area network (WAN), a local area network (LAN), or the Internet, among others. An external computing device may connect to the computer system 800 through the network 812. In some examples, an external computing device may be an external web server or a cloud computing node.

It is to be understood that the block diagram of FIG. 8 is not intended to indicate that the computer system 800 is to include all of the components shown in FIG. 8. Rather, the computer system 800 can include any appropriate fewer or additional components not illustrated in FIG. 8 (e.g., additional memory components, embedded controllers, modules, additional network interfaces, etc.). Further, the aspects described herein with respect to computer system 800 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects.

FIG. 9 depicts a flowchart of a method 900 for low-latency video capture and overlay according to one or more aspects. Method 900 can be executed, for example, by video processing system 300, 600 of FIGS. 3-6, and/or other systems as disclosed herein to perform a computer-implemented method. For purposes of explanation, the method 900 is described in reference to of FIGS. 1-9 and may be performed in an alternate order including adding, removing, combining, or subdividing steps.

At block 902, video capture circuitry 320 of video processing system 300, 600 can receive video input 404 associated with a surgical procedure. At block 904, the video capture circuitry 320 can provide the video input 404 to one or more processing devices of the video processing system 300, 600, such as processing device 304 and/or graphics processing unit 324, to analyze the video input 404. At block 906, an overlay 406 is received from the one or more processing devices, where the overlay 406 is temporally associated with the video input 404, and the overlay 406 can be formed as a composite of one or more sources. Temporal association need not be exact temporal alignment, as differences in latency and update rates or other signal propagation and processing delays may occur. The one or more sources can include a GUI, status information, output of an AI model, a 3-dimensional model, another video source, or other source with an image or video component. At block 908, a blended video output 408 of the surgical procedure is created based on combining the video input 404 with the overlay 406 through a blending function 402. At block 910, the blended video output 408 is output to a primary display 344 as a loopback of the video input 404.

In some aspects, providing the video input 404 to the one or more processing devices can be performed by passing the video input 404 through a multiplexing switch 306 to a graphics processing unit 324. At least a portion of an auxiliary output can be passed back through the multiplexing switch 306 to the blending function 402 using direct memory access or remote direct memory access by a direct memory access controller 350. A second processing device of the one or more processing devices (e.g., processing device 304) can provide surgical data to the multiplexing switch 306, and the overlay 406 can incorporate at least a portion of the surgical data and the auxiliary output. As one example, the graphics processing unit 324 can be configured to generate the auxiliary output, and the auxiliary output can be transmitted to a secondary display 346.

In some aspects, bypassing of the blending function 402 can be performed to route the video input 404 directly to the primary display 344 based on determining that the overlay 406 is inactive.

The video input 404 can be provided to the one or more processing devices by passing the video input 404 through a multiplexing switch 306 to the one or more processing devices. The one or more processing devices can generate the overlay 406 based at least in part on one or more video frames of the video input 404 and/or other data and send the overlay 406 to the blending function 402 through the multiplexing switch 306. A network interface controller module 328 can be configured to communicate with one or more networked devices 342 through the multiplexing switch 306, where data from the networked devices 342 can be transferred to a device coupled to the multiplexing switch 306 and/or data or video can be sent from devices coupled to the multiplexing switch 306 to the networked devices 342. At least one of the one or more networked devices 342 can provide an overlay input to the multiplexing switch 306. A storage device 318 can be configured to store a portion of the blended video output 408 received through an interface 322 between the video capture circuitry 320 and the one or more processing devices, such as processing device 304.

In some aspects, the one or more processing devices are configured make one or more phase predictions associated with the surgical procedure, and the overlay 406 is based on the one or more phase predictions. The overlay 406 can include a reduced-size copy of content output to the secondary display 346. One or more aspects of the overlay 406 can be adjustable through a user interface associated with the primary display 344.

In some aspects, the blended video output 408 can be transmitted to one or more networked devices 342 through multiplexing switch 306 of the video processing system 300, where one or more processing devices are coupled to the multiplexing switch 306. A portion of the blended video output 408 can be streamed to a storage device 318 through the multiplexing switch 306.

FIG. 10 depicts a flowchart of a method 1000 for low-latency video capture and overlay according to one or more aspects. Method 1000 can be executed, for example, by video processing system 300, 600 of FIGS. 3-6, and/or other systems as disclosed herein to perform a computer-implemented method. For purposes of explanation, the method 1000 is described in reference to of FIGS. 1-10 and may be performed in an alternate order including adding, removing, combining, or subdividing steps. The method 1000 can be performed in conjunction with the method 900 of FIG. 9.

At block 1002, video input 404 associated with a surgical procedure can be received and converted to a task-dependent format by the video capture circuitry 320, graphics processing unit 324, and/or processing device 304. As an example, the video input 404 can be received from an endoscopic camera, a robotic camera, or other such camera 105, 204. The video capture circuitry 320, graphics processing unit 324, and/or processing device 304 can perform pre-processing of the video input 404, such as resampling and/or color space conversion. In some aspects, the video capture circuitry 320, graphics processing unit 324, and/or processing device 304 can convert video frames of the video input 404 to a standardized task-dependent format and perform other image manipulation steps. This can include a color space conversion to a pixel-order red-green-blue (RGB) format and resolution change, if necessary, followed by a normalization of the RGB values with a predefined mean and standard variation of the color space. The pre-processing can allow the system to standardize the input video data for further processing, such as applying AI algorithms.

At block 1004, a real-time prediction for a current frame in the task-dependent format can be generated based on information from previous frames. Pre-processed video frames can be encoded into intermediate feature representations as the frames pass through the AI algorithm. The AI algorithm can be designed to use information from previous frames to enhance the prediction for the state of the current frame. This temporal processing provides the AI algorithm with contextual information about the past to produce more temporally coherent predictions. In some aspects, the output of the real-time predictions can be a list of detections, either in the form of coordinates for energy instruments (e.g., centroid or bounding box coordinates) or in the form of probabilistic predictions over a pixel grid for critical structures identification (e.g., probability of a pixel being background versus cystic duct versus cystic artery in the context of laparoscopic cholecystectomy). The AI algorithm can be implemented in software, firmware, or circuitry by the video capture circuitry 320, graphics processing unit 324, and/or processing device 304.

At block 1006, a notification or visualization can be generated as an intermediate overlay image based on the real-time prediction of block 1004. For example, post-processing of an output of the AI algorithm can be performed using a deterministic algorithm to generate the notifications or visualizations depending on the real-time visualization (e.g., images for energy instruments and overlay/heat map for critical structures identification, etc.). The output of post-processing can be one overlay image for each of AI algorithm where multiple AI algorithms are implemented. The intermediate overlay generation can be performed by the video capture circuitry 320, graphics processing unit 324, and/or processing device 304.

At block 1008, the intermediate overlay image of block 1006 can be combined with a GUI to create a final overlay image, such as a combination of overlays 708, 712 of FIG. 7. In some aspects, a multi-step composition approach to generate the final image is used where multiple sources generate overlays. Once the overlays/notifications are generated for each AI algorithm, the overlays can be combined with a GUI rendering into a single overlay, for instance, by an interface compositor function. The combined overlay can be generated at a predetermined frequency for on-screen display with the AI algorithm and/or deterministic algorithm updating independently at a frequency that can differ from the display output frequency.

At block 1010, the video input 404 is blended with the final overlay image of overlay 406 to produce the blended video output 408. The combined overlay can be sent to as overlay 406 as a composition for blending by the blending function 402. The overlay 406 can be blended with the video input 404 (e.g., a loopback image) through the blending function 402. Prior to blending, the overlay 406 may pass through a resampling and/or color space conversion to restore video signal characteristics of pre-processing performed in block 1002. Loopback compositing can prioritize a minimal-latency approach on a live video feed where images from the video input 404 can be immediately composited with the contents of the last received overlay 406, allowing for independent and minimal latency on the live video feed regardless of the time required for the algorithm processing. This asynchronous compositing can limit delays/freezes on primary display 344. Aspects can also include safety watchdog monitors configured to disable the overlay 406 in case of a detected failure condition.

Although the steps of method 1000 are described as being performed by video capture circuitry 320, graphics processing unit 324, and/or processing device 304, it will be understood that additional processing support, memory, and/or circuitry can be used to implement method 1000. For example, portions of the steps of method 1000 can be distributed between multiple processing system resources beyond those depicted in the examples of FIGS. 3-6.

As used herein, "critical anatomical structures" can be specific to the type of surgical procedure being performed and identified automatically. Additionally, a surgeon or any other user can configure the systems described herein to identify particular anatomical structures as critical for a particular patient. The selected anatomical structures are critical to the success of the surgical procedure, such as anatomical landmarks (e.g., Calot triangle, Angle of His, etc.) that need to be identified during the procedure or those resulting from a previous surgical task or procedure (e.g., stapled or sutured tissue, clips, etc.). The systems can access a plurality of surgical objectives associated with the surgical procedure and correlate the surgical objectives with the one or more surgical instruments and the phase of the surgical procedure. Observations relative to critical anatomical structures and surgical objectives can be used to control alert generation. The critical anatomical structures can be used for determining an abnormal event in some examples.

Aspects of the technical solutions described herein can improve CAS systems, particularly by facilitating low-latency video capture and overlay. Further, the technical solutions described herein facilitate improvements to computing technology, particularly computing techniques used for distributed processing, storage, and transmission.

Aspects of the technical solutions described herein facilitate one or more machine learning models, such as computer vision models, to process images obtained from a live video feed of the surgical procedure in real-time using spatio-temporal information. The machine learning models using techniques such as neural networks to use information from the live video feed and (if available) robotic sensor platform to predict one or more features, such as anatomical structures, surgical instruments, in an input window of the live video feed, and further refine the predictions using additional machine learning models that can predict a phase of the surgical procedure. The machine learning models can be trained to identify the surgical phase(s) of the procedure and structures in the field of view by learning from raw image data. When in a robotic procedure, the computer vision models can also accept sensor information (e.g., instruments enabled, mounted, etc.) to improve the predictions. Computer vision models that predict instruments and critical anatomical structures use temporal information from the phase prediction models to improve the confidence of the predictions in real-time.

The predictions and the corresponding confidence scores can be used to generate and display video based on video captured during a surgical procedure. Aspects of the technical solutions described herein provide a practical application in surgical procedures and with low-latency video capture and overlay during surgical procedures.

It should be noted that although some aspects can include endoscopic video, the technical solutions described herein can be applied to analyze video and image data captured by cameras that are not endoscopic (i.e., cameras external to the patient's body) when performing open surgeries (i.e., not laparoscopic surgeries). For example, the video and image data can be captured by cameras that are mounted on one or more personnel in the operating room, e.g., surgeon. Alternatively, or in addition, the cameras can be mounted on surgical instruments, walls, or other locations in the operating room.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to aspects of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present invention have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects described herein.

Various aspects of the invention are described herein with reference to the related drawings. Alternative aspects of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains," or "containing," or any other variation thereof are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general-purpose microprocessors, application-specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A computer-implemented method comprising:
receiving a video input at video capture circuitry of a video processing system, the video input associated with a surgical procedure;
providing the video input to one or more processing devices of the video processing system to analyze the video input, wherein providing the video input to the one or more processing devices comprises passing the video input through a multiplexing switch to a graphics processing unit;
receiving an overlay from the one or more processing devices, the overlay temporally associated with the video input and the overlay formed as a composite from one or more sources;
creating a blended video output of the surgical procedure based on combining the video input with the overlay through a blending function; and
outputting the blended video output to a primary display as a near immediate return of the video input.

2. The computer-implemented method of claim 1, wherein at least a portion of an auxiliary output is passed back through the multiplexing switch to the blending function using direct memory access or remote direct memory access.

3. The computer-implemented method of claim 2, wherein the graphics processing unit is configured to generate the auxiliary output, and the auxiliary output is transmitted to a secondary display.

4. The computer-implemented method of claim 2, wherein a second processing device of the one or more processing devices provides surgical data to the multiplexing switch, and the overlay incorporates at least a portion of the surgical data and the auxiliary output.

5. The computer-implemented method of claim 1, further comprising:

communicating with one or more networked devices through the multiplexing switch, wherein at least one of the one or more networked devices provides an overlay input to the multiplexing switch.

6. The computer-implemented method of claim 1, further comprising:
bypassing the blending function to route the video input directly to the primary display based on determining that the overlay is inactive or an error condition exists.

7. The computer-implemented method of claim 1, wherein the one or more processing devices generate the overlay based at least in part on one or more video frames and/or other data and send the overlay to the blending function through the multiplexing switch.

8. The computer-implemented method of claim 1, further comprising:
converting the video input into an adjusted format;
generating a real-time prediction for a current frame in the adjusted format based on information from one or more previous frames;
generating a notification or visualization as an intermediate overlay image based on the real-time prediction; and
combining the intermediate overlay image with a graphical user interface to create a final overlay image as the overlay.

9. A video processing system comprising:
one or more processing devices;
a primary display interface; and
video capture circuitry configured to perform:
receiving a video input associated with a surgical procedure;
providing the video input to the one or more processing devices to analyze the video input;
receiving an overlay from the one or more processing devices;
creating a blended video output of the surgical procedure based on combining the video input with the overlay; and
outputting the blended video output to a primary display through the primary display interface as a near immediate return of the video input, wherein providing the video input to the one or more processing devices comprises passing the video input through a multiplexing switch to a graphics processing unit configured to generate an auxiliary output to a secondary display and generate at least a portion of the overlay.

10. The video processing system of claim 9, wherein the multiplexing switch is configured to provide the overlay to a blending function using direct memory access or remote direct memory access.

11. The video processing system of claim 10, further comprising a network interface controller module configured to communicate with one or more networked devices through the multiplexing switch, wherein at least one of the one or more networked devices provides an overlay input to the multiplexing switch.

12. The video processing system of claim 9, further comprising:
a storage device configured to store a portion of the blended video output received through an interface between the video capture circuitry and the one or more processing devices.

13. The video processing system of claim 9, wherein the video capture circuitry is configured to bypass blending of the video input with the overlay to route the video input directly to the primary display based on determining that the overlay is inactive or an error condition exists.

14. A computer program product comprising a non-transitory memory device having executable instructions stored thereon, which when executed by a video processing system cause the video processing system to perform:

receiving a video input associated with a surgical procedure at video capture circuitry of the video processing system;

receiving an overlay from one or more processing devices of the video processing system, the overlay temporally associated with the video input;

creating a blended video output of the surgical procedure based on combining the video input with the overlay as a near immediate return of the video input; and generating an auxiliary output based on the overlay, and transmitting the auxiliary output to a secondary display;

outputting the blended video output to a primary display, wherein the video processing system interfaces with the secondary display, and a primary display output of the video processing system has a lower latency than a secondary display output of the video processing system.

15. The computer program product of claim 14, wherein the executable instructions are configured to cause the video processing system to make one or more phase predictions associated with the surgical procedure, and the overlay is based on the one or more phase predictions.

16. The computer program product of claim 14, wherein the overlay comprises a reduced-size copy of content output to the secondary display.

17. The computer program product of claim 14, wherein one or more aspects of the overlay are adjustable through a user interface associated with the primary display.

18. The computer program product of claim 14, wherein the video processing system is configured to perform:

transmitting the blended video output to one or more networked devices through a multiplexing switch of the video processing system, wherein the one or more processing devices are coupled to the multiplexing switch.

19. The computer program product of claim 18, wherein the video processing system is configured to perform:

streaming a portion of the blended video output to a storage device through the multiplexing switch.

20. The computer program product of claim 14, wherein the video processing system is configured to perform bypassing of blending of the video input with the overlay to route the video input directly to the primary display based on determining that the overlay is inactive or an error condition exists.

* * * * *